United States Patent
Stearns

(10) Patent No.: US 8,941,071 B1
(45) Date of Patent: Jan. 27, 2015

(54) METHODS AND SYSTEMS FOR AXIALLY SEGMENTING POSITRON EMISSION TOMOGRAPHY DATA

(71) Applicant: General Electric Company, Schenectady, NY (US)

(72) Inventor: Charles William Stearns, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 50 days.

(21) Appl. No.: 13/945,014

(22) Filed: Jul. 18, 2013

(51) Int. Cl.
    *G01T 1/161* (2006.01)

(52) U.S. Cl.
    CPC ........................... *G01T 1/161* (2013.01)
    USPC ..................................................... 250/363.04

(58) Field of Classification Search
    CPC ........ A61B 5/0073; A61B 6/037; A61B 8/13; G01T 1/161
    USPC ................................................... 250/363.04
    See application file for complete search history.

(56) References Cited

U.S. PATENT DOCUMENTS

| | | | |
|---|---|---|---|
| 6,490,476 B1 * | 12/2002 | Townsend et al. | 600/427 |
| 6,915,004 B2 | 7/2005 | Newport et al. | |
| 7,391,027 B2 | 6/2008 | Kitamura | |
| 8,058,620 B2 * | 11/2011 | Bendriem et al. | 250/363.03 |
| 2005/0129170 A1 * | 6/2005 | Watson et al. | 378/5 |
| 2005/0129295 A1 | 6/2005 | Shanmugam et al. | |
| 2007/0018108 A1 | 1/2007 | Kitamura | |
| 2009/0238337 A1 | 9/2009 | Wang | |
| 2010/0074498 A1 * | 3/2010 | Breeding et al. | 382/131 |
| 2012/0308106 A1 * | 12/2012 | Kelly et al. | 382/131 |

FOREIGN PATENT DOCUMENTS

WO    2014024099 A2    2/2014

OTHER PUBLICATIONS

"Continuous bed motion acquisition on a whole body combined PET/CT system", D. Brasse, et al, IEEE, 20013 pp. 951-955.
"Continuous bed motion data processing for a high resolution LSO PET/CT scanner", Z. Burbar, et al, IEEE, 2005 pp. 2046-2048.
"Continuous bed motion acquisition for an LSO PET/CT scanner", David W. Townsend, et al, IEEE 2004.
Search Report and Written Opinion from Corresponding PCT Application No. PCT/US2014/046092 dated Oct. 8, 2014. 10 pages.

* cited by examiner

*Primary Examiner* — Marcus Taningco
(74) *Attorney, Agent, or Firm* — Dean D. Small; The Small Patent Law Group

(57) ABSTRACT

A method for generating a Positron Emission Tomography (PET) image includes defining a scan window having a predetermined length along an examination axis of a PET imaging system, the scan window corresponding to a region of interest to be continuously scanned by the PET imaging system, defining at least two data bins corresponding to two separate scan regions within the scan window, defining a transition region that overlaps a portion of each of the separate scan regions within the scan window, the transition region having a width that is shorter than a length of the scan window, binning emission data acquired within the transition region into the two data bins, binning emission data acquired from outside the transition region into one of the two data bins, and reconstructing an image using the emission data in the two data bins.

20 Claims, 6 Drawing Sheets

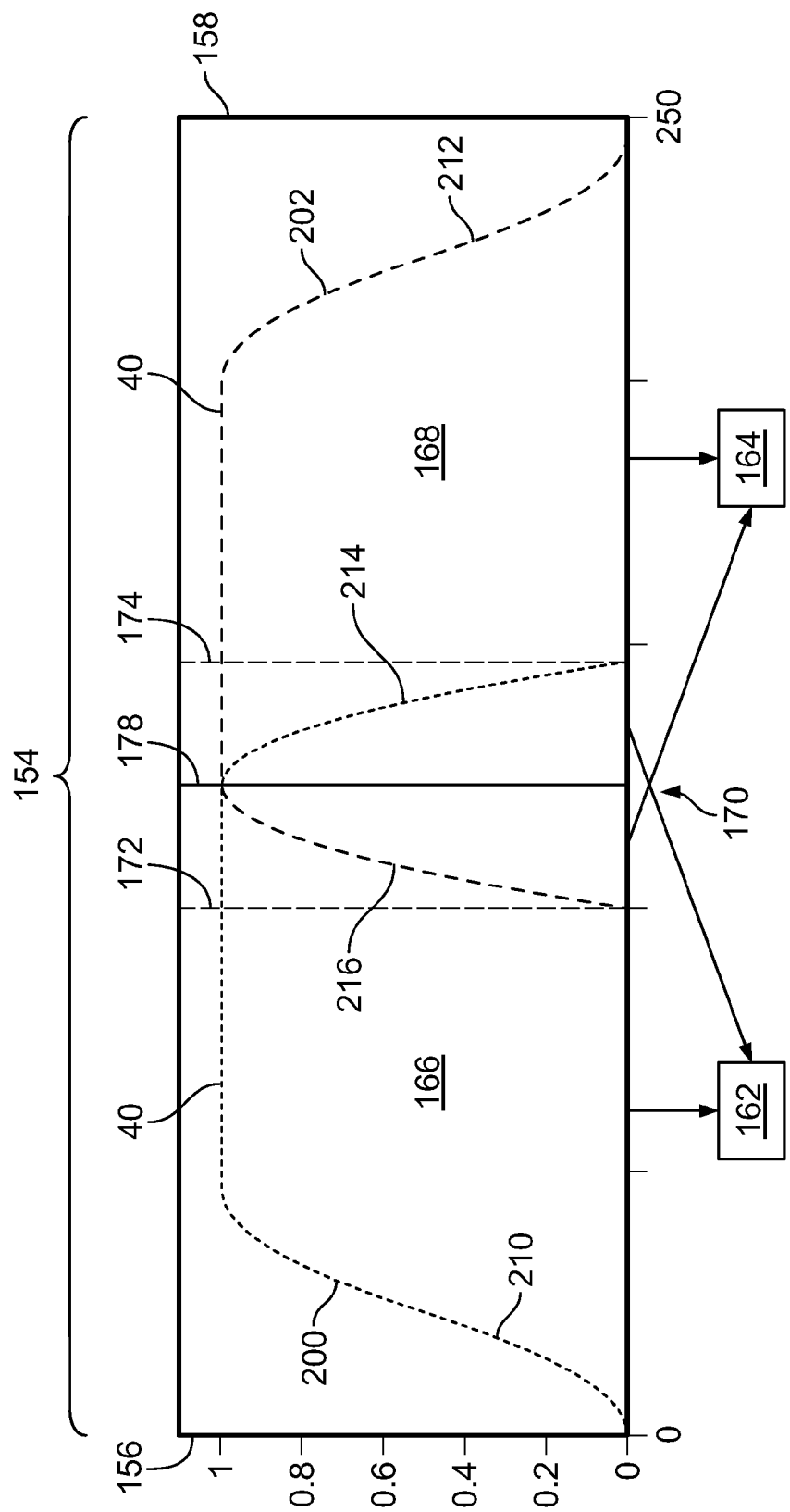

US 8,941,071 B1

METHODS AND SYSTEMS FOR AXIALLY SEGMENTING POSITRON EMISSION TOMOGRAPHY DATA

BACKGROUND OF THE INVENTION

The subject matter disclosed herein relates generally to imaging systems, and more particularly to methods and systems for axially segmenting Positron Emission Tomography (PET) data.

PET systems generate images that represent the distribution of positron-emitting nuclides within the body of a subject 16. When a positron interacts with an electron by annihilation, the entire mass of the positron-electron pair is converted into two 511 keV photons. The photons are emitted in opposite directions along a line of response. The annihilation photons are detected by detectors that are placed along the line of response on a detector ring. When these photons arrive and are detected at the detector elements at the same time, this is referred to as coincidence. An image is then generated based on the acquired emission data includes the annihilation photon detection information.

In operation, at least some known PET systems acquire the emission data using a step-and-shoot method. For example, the subject 16 is positioned at a first axial position within the PET imaging system. Emission data is then acquired at the first axial position. Subsequently, the subject 16 is then moved to a second axial position wherein additional emission data is acquired. Thus, the subject 16 is moved to a plurality of axial positions within the PET imaging system to acquire the emission data.

However, in some instances the sensitivity of the PET detector is not uniform over the entire scan. Thus, the emission data acquired using the step-and-shoot mode of operation may have a non-uniform signal-to-noise ratio (SNR). More specifically, the sensitivity profile may be uneven such that some of the images reconstructed using emission data acquired during the step-and-shoot mode of operation may have inconsistent quality. Moreover, because the emission data is acquired at different individual axial positions, a weighted average must be utilized to perform reconstruction at the area where the images overlap, such that the reconstruction of various frames forming the image is performed one frame at a time.

BRIEF DESCRIPTION OF THE INVENTION

In one embodiment, a method for generating a Positron Emission Tomography (PET) image is provided. The method includes defining a scan window having a predetermined length along an examination axis of a PET imaging system, the scan window corresponding to a region of interest to be continuously scanned by the PET imaging system, defining at least two data bins corresponding to two separate scan regions within the scan window, defining a transition region that overlaps a portion of each of the separate scan regions within the scan window, binning emission data acquired within the transition region into the two data bins, binning emission data acquired from outside the transition region into one of the two data bins, and reconstructing an image using the emission data in the two data bins.

In another embodiment, a Positron Emission Tomography (PET) imaging system is provided. The PET imaging system includes a detector and a processor coupled to the detector. The processor is programmed to receive an input defining a scan window having a predetermined length along an examination axis of the PET imaging system, the scan window corresponding to a region of interest to be continuously scanned by the PET imaging system, define at least two data bins corresponding to two separate scan regions within the scan window, define a transition region that overlaps a portion of each of the separate scan regions within the scan window, bin emission data acquired within the transition region into the two data bins, bin emission data acquired from outside the transition region into one of the two data bins, and reconstruct an image using the emission data in the two data bins.

In a further embodiment, a non-transitory computer readable medium encoded with a program programmed is provided. The non-transitory computer readable medium is programmed to instruct a computer to receive an input defining a scan window having a predetermined length along an examination axis of the PET imaging system, the scan window corresponding to a region of interest to be continuously scanned by the PET imaging system, define at least two data bins corresponding to two separate scan regions within the scan window, define a transition region that overlaps a portion of each of the separate scan regions within the scan window, bin emission data acquired within the transition region into the two data bins, bin emission data acquired from outside the transition region into one of the two data bins, and reconstruct an image using the emission data in the two data bins.

BRIEF DESCRIPTION OF THE DRAWINGS

FIG. 5 is a sensitivity profile generated in accordance with various embodiments.

DETAILED DESCRIPTION OF THE INVENTION

Figure 1:
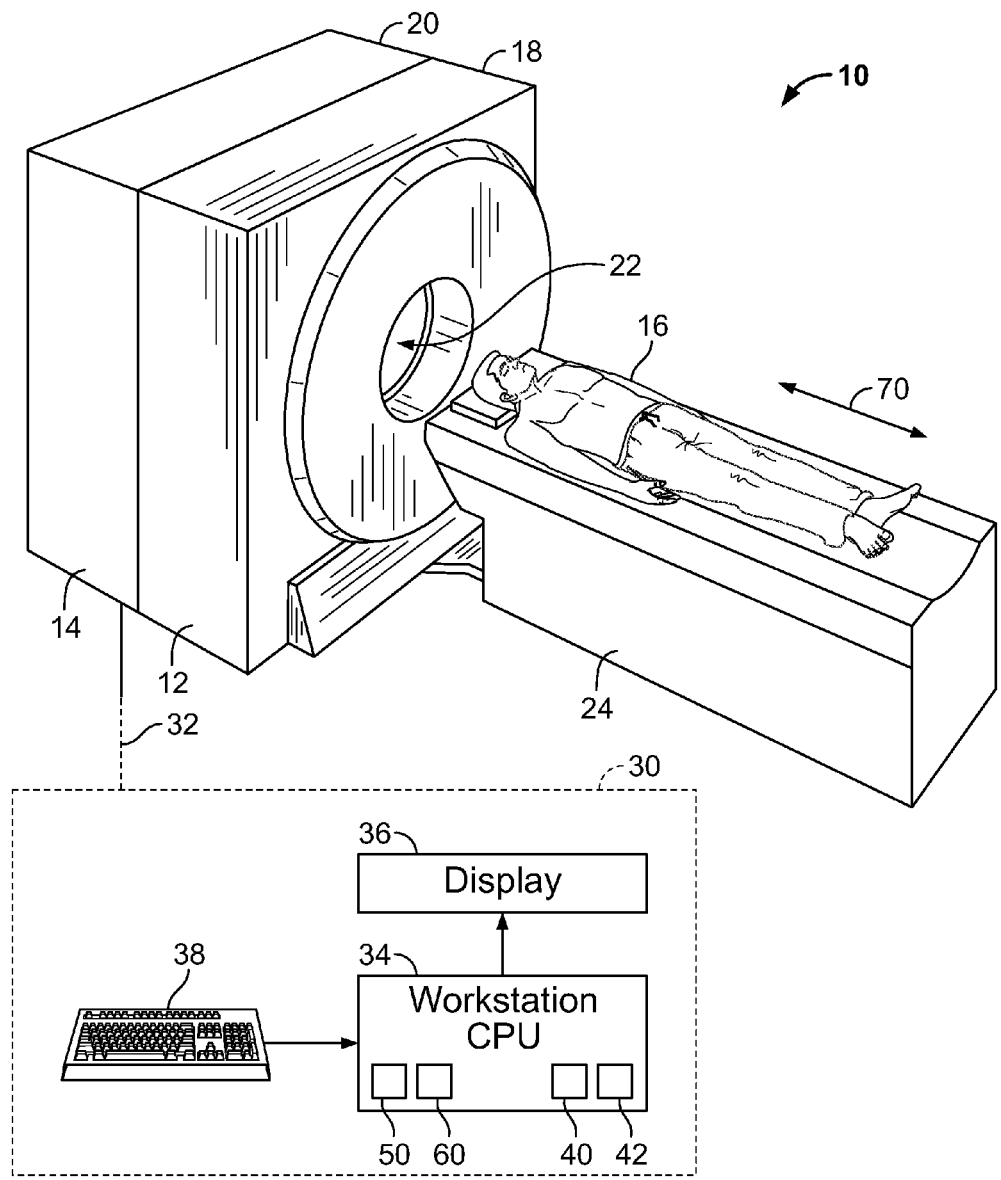
FIG. 1 is a pictorial view of an exemplary imaging system formed in accordance with various embodiments.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for axially segmenting emission data acquired during a continuous table motion (CTM) scan of a region of interest. As used herein, CTM means that the emission data is acquired over a region of interest while the table is continuously moving. Thus, emission data is acquired without interruption over the entire scan period. More specifically, and as explained in more detail below, a scan window having a predetermined length is defined, wherein the scan window corresponds to a region of interest to be continuously scanned by, for example, a Positron Emission Tomography (PET) imaging system. Continuously, as used herein, means that emission data is acquired during the entire scanning procedure whether the table is in motion or stationary. In the illustrated embodiment, the table is moved without interruption during the entire scanning procedure. Thus, the emission data acquired during the scanning procedure is also continuous, meaning that the emission data does not have any interruptions, gaps, and/or pauses.

In operation, at least two data bins corresponding to two separate scan regions within the scan window are then defined such that a transition region overlaps a portion of each of the separate scan regions within the scan window. Accordingly, in operation as a detector approaches the transition region, all of the emission data is stored within the first bin, or subset, and none of the emission data is stored in the second bin, or subset. As the detector passes into the transition region, all of the emission data is stored in the first bin and an increasing amount of emission data is stored in the second bin. At a center of the transition region substantially all of the emission data is stored in both the first and second bins. As the detector continues past the center point, all of the emission data is stored in the second bin, while a decreasing amount of the emission data is stored in the first bin. As the detector exits the transition region, the amount of emission data stored in the first bin is gradually reduced to zero and all of the emission data is then stored in the second bin exclusively.

Thus, the emission data in the first bin forms a first data subset and the emission data stored within the second bin forms a second data subset. The resulting data subsets have the same configuration as a full CTM data set, e.g. a single dataset acquired over the entire length of the scan window. As a result, after the first data subset is completed, the system may be configured to reconstruct an image using the emission data in the first data subset while concurrently storing data in the second data subset. In this manner, the overall time to reconstruct an image is reduced.

The methods described herein may be implemented using an imaging system such as the imaging system 10 shown in FIG. 1. In various embodiments, the imaging system 10 is a multi-modality imaging system that includes different types of medical imaging systems, such as a Positron Emission Tomography (PET), a Single Photon Emission Computed Tomography (SPECT), a Computed Tomography (CT), an ultrasound system, a Magnetic Resonance Imaging (MRI) or any other system capable of generating diagnostic images. In the illustrated embodiment, the imaging system 10 is a PET/CT system. It should be realized that the various embodiments are not limited to multi-modality medical imaging systems, but may be used on a single modality medical imaging system such as a stand-alone PET imaging system or a stand-alone SPECT system, for example. Moreover, the various embodiments are not limited to medical imaging systems for imaging human subjects, but may include veterinary or non-medical systems for imaging non-human objects, etc.

Referring to FIG. 1, the multi-modality imaging system 10 includes a first modality unit 12 and a second modality unit 14. The two modality units enable the multi-modality imaging system 10 to scan an object or subject 16 in a first modality using the first modality unit 12 and to scan the subject 16 in a second modality using the second modality unit 14. The multi-modality imaging system 10 allows for multiple scans in different modalities to facilitate an increased diagnostic capability over single modality systems. In the illustrated embodiment, the first modality 12 is a PET imaging system and the second modality 14 is a CT system. The imaging system 10 is shown as including a gantry 18 that is associated with the PET imaging system 12 and a gantry 20 that is associated with the CT system 14. During operation, the subject 16 is positioned within a central opening 22, defined through the imaging system 10, using, for example, a motorized table 24.

The imaging system 10 also includes an operator workstation 30. During operation, the motorized table 24 moves the subject 16 into the central opening 22 of the gantry 18 and/or 20 in response to one or more commands received from the operator workstation 30. The workstation 30 then operates the first and/or second modalities 12 and 14 to both scan the subject 16 and to acquire PET emission data 40 and/or CT data 42 of the subject 16. The workstation 30 may be embodied as a personal computer (PC) that is positioned near the imaging system 10 and hard-wired to the imaging system 10 via a communication link 32. The workstation 30 may also be embodied as a portable computer such as a laptop computer or a hand-held computer that transmits information to, and receives information from the imaging system 10. Optionally, the communication link 32 may be a wireless communication link that enables information to be transmitted to and/or from the workstation 30 to the imaging system 10 wirelessly. In operation, the workstation 30 is configured to control the operation of the imaging system 10 in real-time. The workstation 30 is also programmed to perform medical image diagnostic acquisition and reconstruction processes described herein.

The operator workstation 30 includes a central processing unit (CPU) or computer 34, a display 36, and an input device 38. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 34 executes a set of instructions that are stored in one or more storage elements or memories, in order to process information received from the first and second modalities 12 and 14. The storage elements may also store data or other information as desired or needed. The storage element may be in the form of an information source or a physical memory element located within the computer 34.

The imaging system 10 also includes an axial segmentation module 50 that is configured to implement various methods described herein. In some embodiments, the axial segmentation module 50 is configured to receive an input that defines a scan window having a predetermined length and receive an input that defines or separates the scan window into at least two scanning regions that are described in more detail below.

In operation, the axial segmentation module 50 is then configured to store the emission data 40 into bins based on the received inputs.

The axial segmentation module 50 may be implemented as a piece of hardware that is installed in the computer 34. Optionally, the axial segmentation module 50 may be implemented as a set of instructions that are installed on the computer 34. Moreover, the set of instructions may be stored on a non-transitory computer readable medium that is configured to be utilized by the computer 34. The set of instructions may be stand alone programs, may be incorporated as subroutines in an operating system installed on the computer 34, may be functions in an installed software package on the computer 34, and the like. It should be understood that the various embodiments are not limited to the arrangements and instrumentality shown in the drawings.

The set of instructions may include various commands that instruct the computer 34 as a processing machine to perform specific operations such as the methods and processes of the various embodiments described herein. The set of instructions may be in the form of a software program or the non-transitory computer readable medium. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
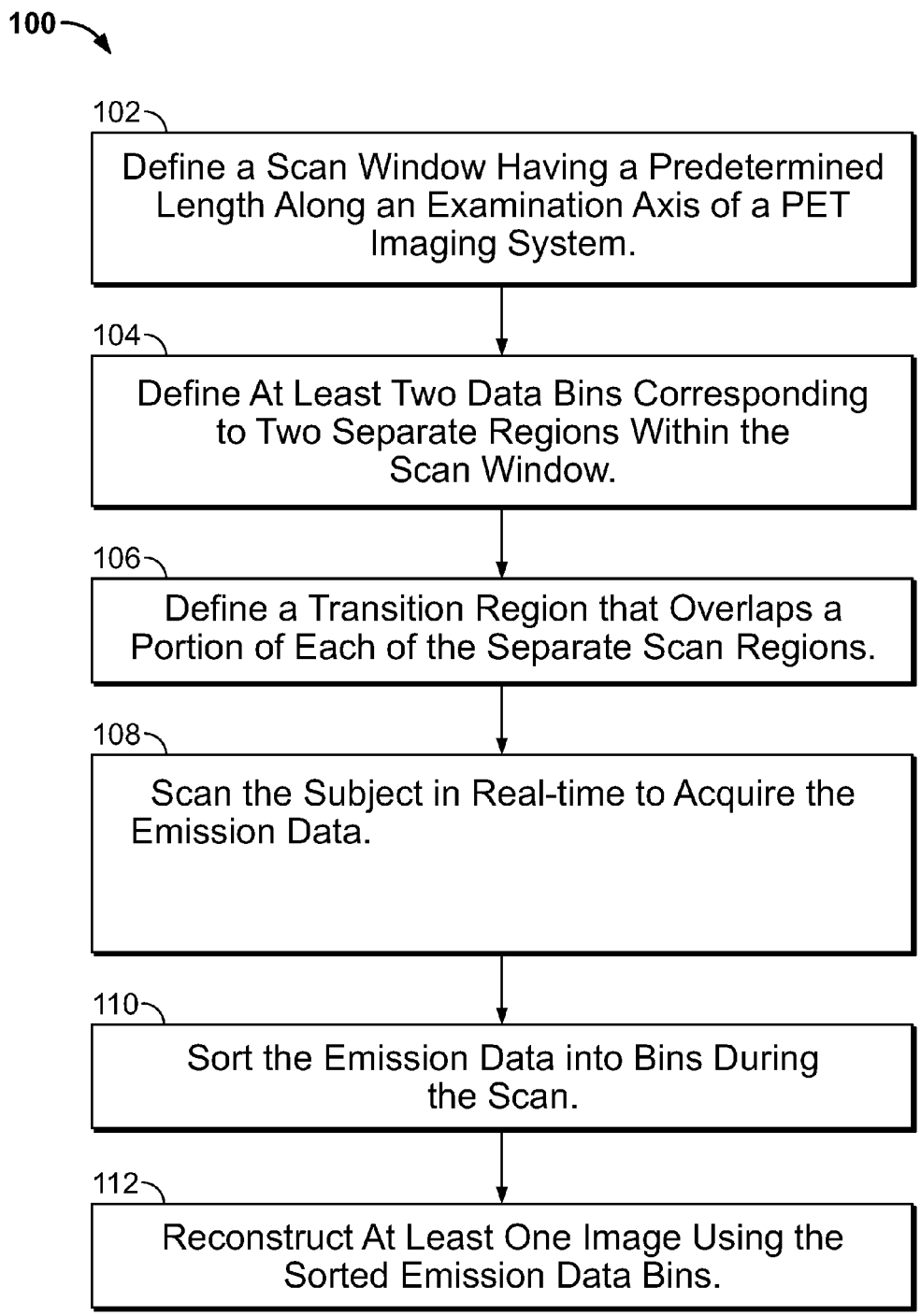
FIG. 2 is a flowchart illustrating a method for generating an image of an object of interest in accordance with various embodiments.

FIG. 2 is a flowchart of an exemplary method 100 for generating a PET image of an object of interest, such as the subject 16 shown in FIG. 1.

Figure 3:
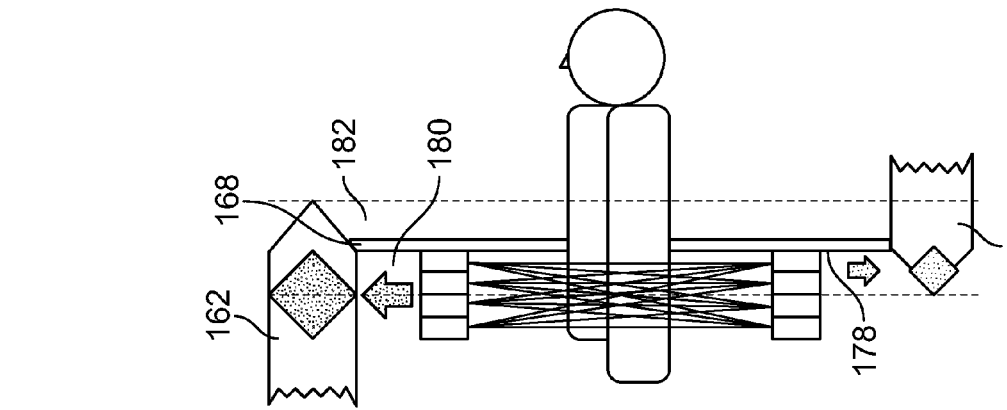
FIG. 3 is illustrates a portion of an exemplary imaging system formed in accordance with various embodiments.

At 102, a scan window 152 having a predetermined length along an examination axis of a PET imaging system is defined. As used herein, the term scan window refers to the portion of the patient being imaged. Thus, the scan window 152 may extend the entire length of the patient for a full body scan, over a portion of the patient for a torso scan, etc. For example, and referring to FIG. 3, in operation, the subject 16 is moved along an examination axis 150 via the table 24 shown in FIG. 1. In the illustrated embodiment, the examination axis 150 extends along a z-axis 70 of the PET system 12 shown in FIG. 1, which is substantially parallel with the movement of the table 24 through the PET system 12. In various embodiments, the scan window 152 is also defined along the z-axis 70. As used herein, a scan window is a distance that the subject 16 moves along the z-axis, within the PET system 12 to continuously acquire the emission data 40. Therefore, it should be realized that the scan window 152 may have any length that enables the operator to acquire diagnostic information of the subject 16. For example, and as shown in FIG. 3, the scan window 152 has a length 154 that extends from a first position 156 to a second position 158. The length 154 of the scan window 152 may be set such that the scan window 152 encompasses the entire subject 16, referred to herein as a whole body scan. Moreover, the length 15 of the scan window 152 may be reduced such that the scan window 152 encompasses only a portion of the subject 16. For example, and as shown in FIG. 3, the length 154 of the scan window 152 is set such that emission data 40 is acquired from the torso area of the subject 16. In various embodiments, the length 154 of the scan window 152 may be set automatically by the axial segmentation module 50 or the computer 34. Optionally, the length 154 of the scan window 152 may be entered manually be an operator into the axial segmentation module 50 and/or the computer 34

At 104, at least two data bins 162 and 164 corresponding to the two separate scan regions 166 and 168 within the scan window are defined. As used herein, a data bin is a space or repository in memory, or other computer device, that is configured to receive and store emission data therein. Thus, in operation, as the emission data 40 is acquired in real-time from a detector 160 shown in FIG. 6, portions of the emission data 40 are stored in at least one of the two data bins 162 and 164 as shown in FIG. 3. The methods of acquiring and storing the emission data 40 into the bins 162 and 164 is described in more detail below. It should be realized that while the illustrated embodiment describes the emission data 40 being stored in two bins, e.g. bins 162 and 164, the emission data 40 may be stored in more than two bins as described in more detail below. In various embodiments, the quantity of bins is set equal to the quantity of scan regions. For example, in the illustrated embodiment, the scan window 152 is divided into two separate scan regions, i.e. regions 166 and 168. Thus, in the illustrated embodiment, the emission data 40 is stored into two bins, i.e. bins 162 and 164. Therefore, it should be realized that if the scan window 152 is divided into three scan regions, three bins are utilized to store the emission data 40, etc.

At 106, a transition region 170 that overlaps a portion of each of the separate scan regions 166 and 168 within the scan window 152 is defined. More specifically, and referring again to FIG. 3, the transition region 170 has a first side 172, a second side 174, and a width 176. Moreover, the transition region 170 has a centerpoint 178 that is positioned approximately halfway between the first and second sides 172 and 174, respectively. The width 176 of the transition region 170 is selected to enable portions of the transition region 170 to overlap at least a portion of the scan regions 166 and 168. In various embodiments, the width 176 of the transition region 170 and/or a location of the centerpoint 178 may be set automatically by the axial segmentation module 50 or the computer 34. Optionally, the width 176 of the transition region 170 and/or a location of the centerpoint 178 may be input manually by the operator into the axial segmentation module 50 and/or the computer 34.

In operation, the centerpoint 178 is defined approximately midway between the first and second sides 172 and 174 of the transition region 170. Thus, the centerpoint 178 also defines a separation between the two separate scan regions 166 and 168. In various embodiments, the centerpoint 178 is positioned such that a width 184 of the first scan region 166 is substantially the same as a width 186 of the second scan region 168. However, it should be realized that the centerpoint 178 may be positioned anywhere along the length 154 of the scan window 152 provided that there is enough room for the transition region 170 to be fitted around the centerpoint 178.

For example, the centerpoint 178 may be positioned such that the first scan region 166 is smaller or larger of than the second scan region 168. In various embodiments, the width 176 of the transition region 170 is less than the length 154 of the scan window 152. For example, the width 176 of the transition region 170 may be 10%, 15%, 20%, etc. of the length 154 of the scan window 152. In the exemplary embodiment, the width 176 of the transition region 170 is approximately twice a width of the axial field-of-view (FOV) of the detector 160. For example, assume that the detector 160 has an axial FOV=N, then the width 176 of the transition region 170≈2N.

In various embodiments, the first side 172, the second side 174, and the centerpoint 178 function to divide the transition region 170 into two separate portions or sub-regions 180 and 182. More specifically, the first transition sub-region 180 is defined between the first side 172 of the transition region 170 and the centerpoint 178. Moreover, the second transition sub-region 182 is defined between the centerpoint 178 and the second side 174 of the transition region 170. In the exemplary embodiment, because the centerpoint 178 is positioned approximately midway between the first and second sides 172 and 174 of the transition region 170, the width of the first transition sub-region 180 is approximately the same as the width of the second transition sub-region 182.

In operation, after the scan window 152 has been defined at 102, the data bins have been defined at 104, and the scan region 170 has been defined at 106, the method proceeds to 108 wherein, the subject 16 is continuously scanned in real-time to acquire the emission data 40. Moreover, at 110, the emission data 40 is sorted or binned into bins e.g. the bins 162 and 164 during the scanning procedure being conducted at 108. In various embodiments, the emission data 40 has a diamond-shaped region in z-theta space, wherein z represents the coordinates along the z-axis 70 and theta (θ) represents an angle between the z-axis 70, along a line of response (LOR) to the detector 160. Thus, at theta=0, a range of v values corresponding to the full axial field of view of the detector 160 are acquired. Moreover, as theta increases or decreases from zero, fewer values of z are available. In operation, the diamond shaped emission data 40 is translated in the z-direction as the table 24 moves through the gantry 12 and the emission data 40 is added together at each (z,θ) location as the diamond moves through. Thus, the resulting emission data 40 has a hexagonal shape in v-theta space.

The overall operation of the PET system 12 is now described with respect to FIG. 4. FIG. 4 illustrates a series of diagrams showing the position of the subject 16 with respect to the detector 160 during an exemplary CTM scanning procedure to acquire the emission data 40.

Figure 4A:
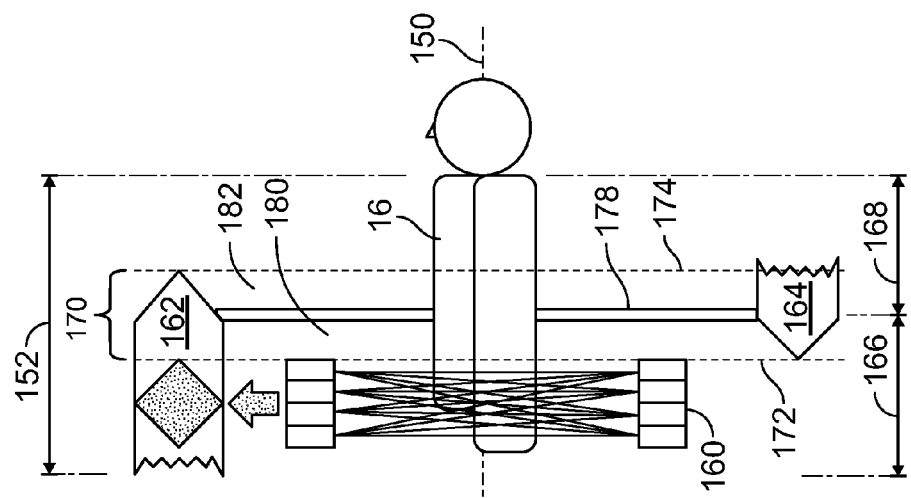
FIG. 4 is a diagrammatic illustration of method of binning emission data in accordance with various embodiments.

Initially, the subject 16 is positioned on the table 24 (shown in FIG. 4A). In the illustrated embodiment, the detector 16 is maintained in a stationary position and the subject 16 moves from the left to the right, via the table 24, such that the subject's feet initially enter the scan window 152 as shown at 200. However, it should be realized that table 24 may be maintained in a stationary position, and the detector 160 may be repositioned to scan the subject 16 as described above. Moreover, it should further be realized that the subject 16 may be placed in any position on the table 24 to perform the scan.

As shown in FIG. 4A, the subject 16 is initially moved within the scan window 152. More specifically, the subject 16 is moved into the first scan region 166 defined within the scan window 152. In various embodiments, while the subject 16 is within the first scan region 166 and outside of the transition region 170, the emission data 40 is stored exclusively in the first data bin 162. As used herein, emission data the term outside refers to any emission data that is not acquired within the transition region 170. For example, emission data 40 acquired between the first side 156 of the scan window 150 and the first side 172 of the transition region 170 is considered to be emission data that is acquired outside of the transition region 170. Similarly, emission data 40 acquired between the second side 158 of the scan window 150 and the second side 172 of the transition region 170 is considered to be emission data that is acquired outside of the transition region 170. Accordingly, emission data that is not acquired within the transition region 170 is considered to be outside the transition region 170.

Figure 4B:
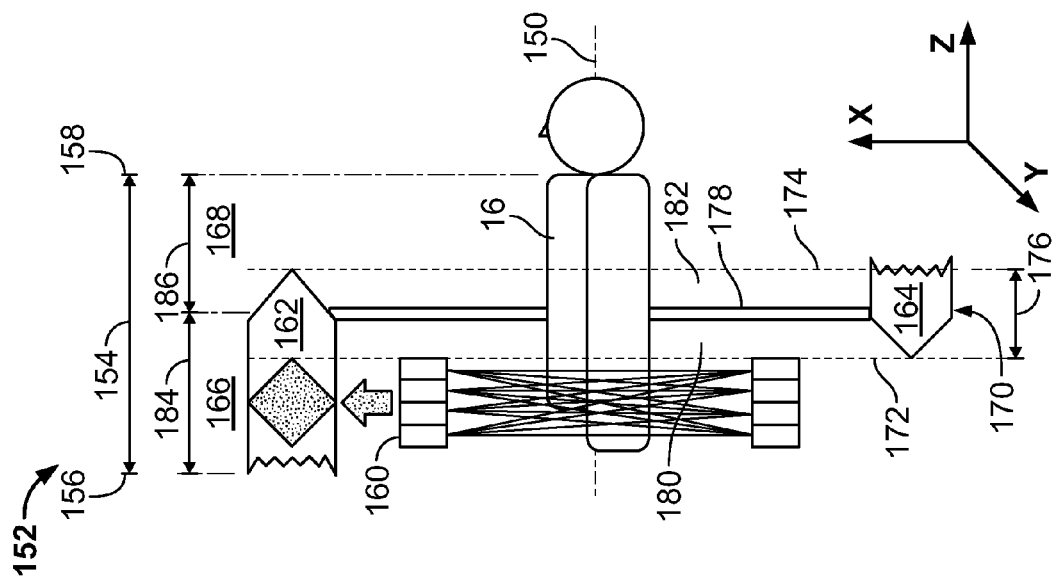
Figure 4E:
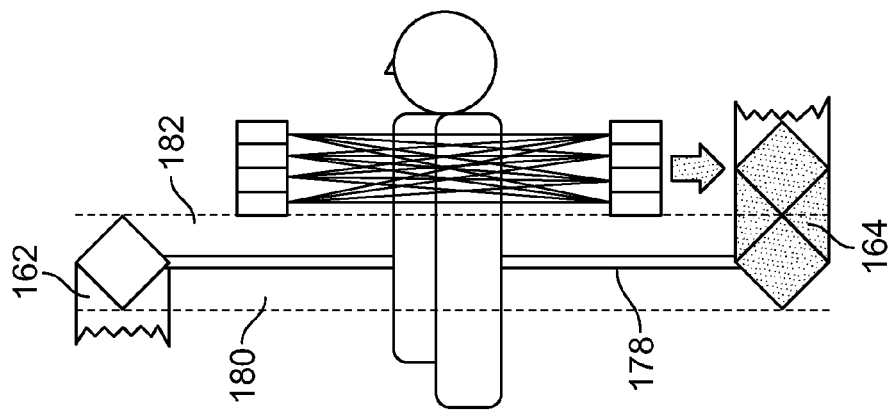

In operation, while the subject 16 is on the left side of the transition region 170, the emission data 40 is stored exclusively within the first data bin 162. As shown in FIGS. 4B and 4C, the subject 16 is then moved through the transition region 170. While the subject 16 is within the transition region 170, the emission data 40 is stored in both the first data bin 162 and the second data bin 164. More specifically, when the subject 16 is between the first side 172 of the transition region 170 and the centerpoint 178 of the transition region 170, the emission data 40 is stored in the first data bin 162. Additionally, at least some of the emission data 40 is stored in the second data bin 164.

In the exemplary embodiment, the quantity of emission data 40 stored in the second bin 164 while the subject 16 is between the first side 172 of the transition region 170 and the centerpoint 178 of the transition region 170 gradually increases from the first side 172 to the centerpoint 178. More specifically, as the subject 16 is moved through the transition region 170 from the first side 172 to the centerpoint 178, the quantity of emission data 40 stored in the second data bin 164 gradually increases while all of the emission data 40 is still being stored in the first data bin 162. When the subject 16 is proximate to the centerpoint 168, substantially all of the emission data 40 is stored in both the first and second data bins 162 and 164, respectively. Thus, the first data bin 162 includes all of the emission data 40 acquired while scanning the first scanning region 166 and the second data bin 164 includes the emission data 40 acquired while scanning the first transition sub-region 180.

Figure 4D:
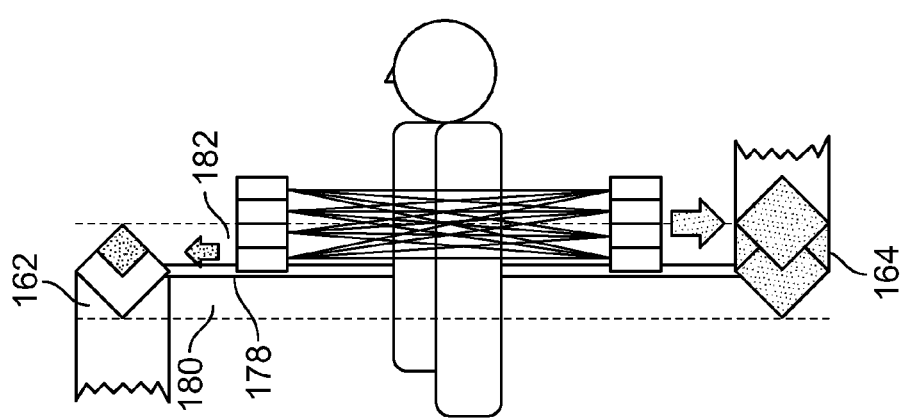
Figure 4C:
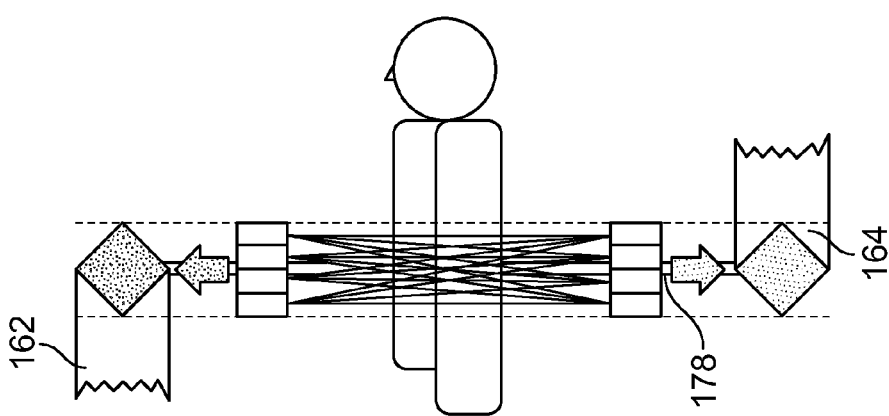

As shown in FIG. 4D, the subject 16 is then moved into the second scan region 168 defined within the scan window 152. In various embodiments, while the subject 16 is within the second scan region 168, the emission data 40 is stored in the second data bin 164. Moreover, when the subject 16 is between the centerpoint 178 and the second side 174 of the transition region 170, the emission data 40 is stored in the second data bin 164. Additionally, at least some of the emission data 40 is stored in the first data bin 162. While the subject 16 is on the right side of the transition region 170, i.e. within the second scanning region 168, the emission data 40 is store exclusively within the second data bin 164.

In the exemplary embodiment, the quantity of emission data 40 stored in the first data bin 162 while the subject 16 is between the centerpoint 168 of the transition region 170 and the second side 174 of the transition region 170 gradually decreases from the centerpoint 168 to the second side 174. More specifically, and as shown in FIGS. 4D and 4E, as the subject 16 is moved through the transition region 170 from the centerpoint 168 to the second side 174, the quantity of emission data 40 stored in the first bin 162 gradually decreases while all of the emission data 40 is still being stored in the second data bin 164. When the subject 16 exits the transition region 170, and is still within the second scanning region 168 all of the emission data 40 is stored within the second data bin 164. Thus, while the subject 16 is within the transition region 170, a portion of the emission data 40 acquired while scanning the first scanning region 166 is stored in the second data bin 164. Similarly, while the subject 16 is within the transition region 170, a portion of the emission data acquired while scanning the second scanning region 168 is stored in the first data bin 162.

In this manner, the first and second data bins 162 and 164, respectively, each include emission data 40 that extends across each scanning region 166 and 168. For example, FIG. 5 is a graphical illustration of the emission data 40 acquired during a scanning procedure as described above wherein the left side of the graph is the first position 156, or first side of the scan window 154, and the right side of the graph is the second position 158, or second side of the scan window 154. As shown in FIG. 5, the first data bin 162 includes all the emission data 40 acquired while scanning the first scanning region 166 and also a portion of the emission data 40 that is adjacent to the first scanning region 166, and within the transition region 170, that is acquired while scanning the second scanning region 168. Similarly, the second data bin 164 includes all the emission data 40 acquired while scanning the second scanning region 168 and also a portion of the emission data 40 that is within the transition region 170 that is acquired while scanning the first scanning region 166.

In operation, and as described above, at any particular time in the scanning procedure, the PET imaging system 10 acquires emission data 40 having a diamond-shaped region in v-theta space. As a result, a full three-dimensional reconstruction of the emission data 40 utilizes the full emission data set. More specifically, because the emission data 40 is acquired continuously during the scanning procedure, there are no gaps or discontinuities in the emission data 40 throughout the scan window 150. Moreover, in various embodiments, the emission data 40 is subdivided into separate bins. Thus, during a scanning procedure that has a relatively long duration, such as a torso scan or a whole-body scan, the reconstruction process may be initiated prior to the completion of the scanning procedure. Additionally, the CTM scanning procedure may be utilized in conjunction with respiratory gating, for example when scanning the thorax and upper abdomen where the effects of respiratory motion are greatest.

Accordingly, in various embodiments described herein the emission dataset 40 is subdivided during the acquisition such that a portion of the emission data 40 is stored in the first data bin 162 and second data bins concurrently. The emission data 40 may be stored within both data bins 162 and 164 when the subject 16 is within a transition region 170 that has a width 176 that is approximately equal to twice the axial extent of the detector 160. Each data bin 162 and 164 then receives emission data 40 which corresponds to (z,θ) coordinates consistent with a full CTM data set ending at the centerpoint 178 as described previously.

As a result, the data bins 162 and 164 have the same configuration as a full CTM data set, and of the subsets, e.g. the data bins 162 and 164, as the emission data acquired during a step-and-shoot scanning procedure. Moreover, the data bins 162 and 164 described herein have a different sensitivity profile because emission data 40 acquired during the transition region 170 is not available during a step-and-shoot scanning procedure. For example, FIG. 5 illustrates an exemplary sensitivity profile for the axial segmentation method described herein wherein a first sensitivity profile 200 and a second sensitivity profile 202 correspond to the first and second data bins 162 and 164 described above. More specifically, a left side 210 of the first sensitivity profile 200 and a right side 212 of the second sensitivity profile 202 illustrate an exemplary sensitivity profile for the beginning and end of the CTM scanning procedure, e.g. from the first side 156 of the scan window 150 to the second side of the scan window 150. Additionally, the portions 214 and 216 of the sensitivity profiles 200 and 202, respectively show the sensitivity profile produced by the axial segmentation method described herein. Thus, each subset of emission data, i.e. data bins 162 and 164, retains its full sensitivity up to the centerpoint 178 of the transition region 170. Accordingly, at least one image may be reconstructed using slices within the data bins 162 and 164 that correspond to the full sensitivity (and therefore lowest noise) portions of the sensitivity profile.

Referring again to FIG. 2, at 112 the emission data 40 is sorted or binned into bins e.g. the bins 162 and 164 during the scan are used to reconstruct an image of the subject 16. In operation, the CTM PET acquisitions blend together the PET emission data 40 acquired as the table 14 moves the subject 16 continuously through the scanner (or, equivalently, as the detector 160 moves along the subject 16 to form a single emission dataset 40 for reconstruction of an axial segment of the subject 16's body. In various embodiments, the full axial extent of the emission data 40 is subdivided sub-segments, e.g. the bins 162 and 164 to enable an image to be reconstructed prior to the completion of the scanning procedure, or to switch acquisition modes from static to gated or vice versa. In various embodiments, the emission data 40 may be subdivided into the bins 162 and 164 by defining contiguous CTM data regions, e.g. the first and second scanning regions 166 and 168. In data space, the first and second scanning regions 166 and 168 overlap, via the transition region 170, and counts corresponding to the first and second scanning regions 166 and 168 of the data space are used in multiple sub-segments. Each scanning region 166 and/or 168 may then be acquired in its desired mode (static or gated), and processed independently. Thus, there is no need to combine the results from different scanning regions (as is the case in traditional step-and-shoot whole-body PET imaging).

The methods described herein therefore provide several advantages. More specifically, CTM data acquisition enables image reconstruction to be broken into several pieces, allowing fully three-dimensional processing of the first data bin 162 to commence (and possibly complete) before the subsequent second data bin 164 is acquired. Moreover, the methods described herein enable gated acquisition to be used only in those portions of the CTM acquisition where it is desired, such as the thorax and upper abdomen for studies to compensate for respiratory motion. It should be appreciated that during gated acquisition full-fidelity images may be acquired without data averaging which is an advantage, in that the averaging of the non-gated slices from one data bin with the gated slices of the other data bin would pose a number of problems.

Figure 6:
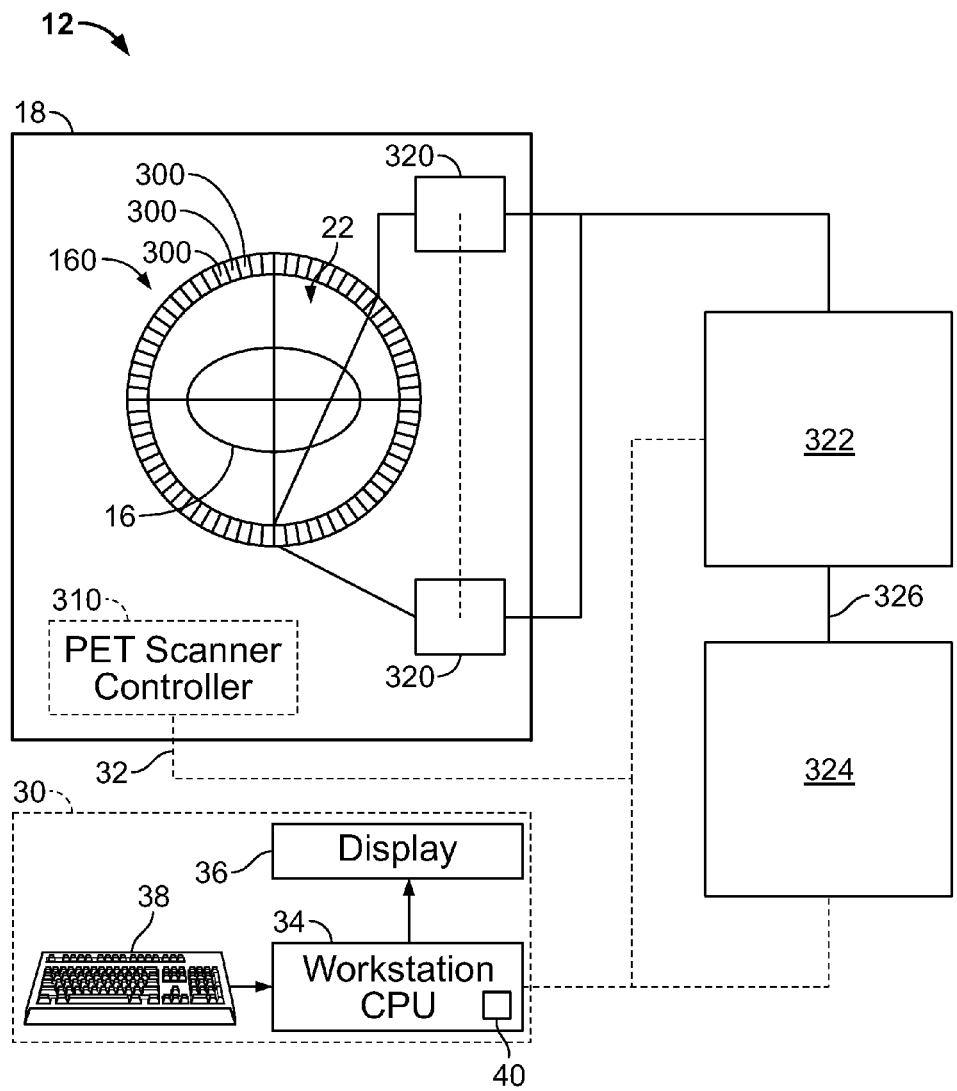
FIG. 6 is a block schematic diagram of the first modality unit shown in FIG. 1 in accordance with various embodiments.

Various embodiments of the methods and the axial segmentation module 40, described herein may be provided as part of, or used with, a medical imaging system, such as a dual-modality imaging system 10 as shown in FIG. 1. FIG. 6 is a block schematic diagram of the second modality unit 12, e.g. the PET imaging system, shown in FIG. 1. As shown in FIG. 6, the PET system 12 includes the detector array 160 that is arranged as ring assembly of individual detector modules 300. The detector array 160 also includes the central opening 22, in which an object, such as the subject 16 may be positioned, using, for example, the motorized table 24 (shown in FIG. 1). The motorized table 24 is aligned with the central axis of the detector array 160. During operation, the motorized table 24 moves the subject 16 into the central opening 22 of the detector array 160 in response to one or more commands received from the operator workstation 30. More specifically, a PET scanner controller 310 responds to the commands received from the operator workstation 30 through the communication link 32. Therefore, the scanning operation is controlled from the operator workstation 30 through PET scanner controller 310.

During operation, when a photon collides with a scintillator on the detector array 160, the photon collision produces a scintilla on the scintillator. The scintillator produces an analog signal that is transmitted to an electronics section (not shown) that may form part of the detector array 160. The electronics section outputs an analog signal when a scintillation event occurs. A set of acquisition circuits 320 is provided to receive these analog signals. The acquisition circuits 320 process the analog signals to identify each valid event and provide a set of digital numbers or values indicative of the identified event. For example, this information indicates when the event took place and the position of the scintillation scintillator that detected the event.

The digital signals are transmitted through a communication link, for example, a cable, to a data acquisition controller 322. The data acquisition processor 322 is adapted to perform the scatter correction and/or various other operations based on the received signals. The PET system 12 may also include an image reconstruction processor 324 that is interconnected via a communication link 326 to the data acquisition controller 322. During operation, the image reconstruction processor 324 performs various image enhancing techniques on the digital signals and generates an image of the subject 16.

As used herein, a set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for generating a Positron Emission Tomography (PET) image, said method comprising:
    defining a scan window having a predetermined length along an examination axis of a PET imaging system, the scan window corresponding to a region of interest to be continuously scanned by the PET imaging system;
    defining at least two data bins corresponding to two separate scan regions within the scan window;
    defining a transition region that overlaps a portion of each of the two separate scan regions, the transition region having a width that is shorter than a length of the scan window;
    binning emission data acquired within the transition region into the two data bins;
    binning emission data acquired from outside the transition region into one of the two data bins; and
    reconstructing an image using the emission data in the two data bins.

2. The method of claim 1, further comprising reconstructing the image using the emission data within a first bin while concurrently binning emission data into a second different bin.

3. The method of claim 1, wherein the transition region includes a first side, a second side, and a centerpoint, said method further comprising:
    binning the emission data acquired to the left of the transition region into a first data bin; and
    binning a portion the emission data acquired between the first side and the centerpoint of the transition region into the first data bin and the second data bin.

4. The method of claim 3, further comprising gradually increasing a quantity of emission data binned into the second data bin from the first side to the centerpoint of the transition region.

5. The method of claim 1, wherein the transition region includes a first side, a second side, and a centerpoint, said method further comprising:
    binning the emission data acquired to the right of the transition region into a second data bin; and
    binning a portion the emission data acquired between the centerpoint and the right side of the transition region into the first data bin and the second data bin.

6. The method of claim 5, further comprising gradually decreasing a quantity of emission data binned into the first data bin from the centerpoint to the second of the transition region.

7. The method of claim 1, wherein the transition region includes a first transition sub-region and a second transition sub-region, said method further comprising:
    binning the emission data acquired to the left of the transition region into a first data bin;
    binning the emission data acquired to the right of the transition region into a second data bin;
    binning a portion of the emission data acquired in the first transition sub-region into the first and second data bins; and
    binning a portion of the emission data acquired in the second transition sub-region into the first and second data bins.

8. The method of claim 1, wherein the transition region has a width that is approximately twice the axial field-of-view of a detector acquiring data from the region of interest.

9. A Positron Emission Tomography (PET) imaging system comprising:
- a detector; and
- a processor coupled to the detector, the processor programmed to
  - receive an input defining a scan window having a predetermined length along an examination axis of the PET imaging system, the scan window corresponding to a region of interest to be continuously scanned by the PET imaging system;
  - define at least two data bins corresponding to two separate scan regions within the scan window;
  - define a transition region that overlaps a portion of each of the separate scan regions within the scan window, the transition region having a width that is shorter than a length of the scan window;
  - bin emission data acquired within the transition region into the two data bins;
  - bin emission data acquired from outside the transition region into one of the two data bins; and
  - reconstruct an image using the emission data in the two data bins.

10. The PET imaging system of claim 9, wherein the processor is further programmed to reconstruct the image using the emission data within a first bin while concurrently binning emission data into a second different bin.

11. The PET imaging system of claim 9, wherein the transition region includes a first side, a second side, and a centerpoint, the processor further programmed to:
- bin the emission data acquired to the left of the transition region into a first data bin; and
- bin a portion the emission data acquired between the first side and the centerpoint of the transition region into the first data bin and the second data bin.

12. The PET imaging system of claim 11, wherein the processor is further programmed to gradually increase a quantity of emission data binned into the second data bin from the first side to the centerpoint of the transition region.

13. The PET imaging system of claim 9, wherein the transition region includes a first side, a second side, and a centerpoint, said processor further programmed to:
- bin the emission data acquired to the right of the transition region into a second data bin; and
- bin a portion the emission data acquired between the centerpoint and the right side of the transition region into the first data bin and the second data bin.

14. The PET imaging system of claim 13, wherein the transition region includes a first side, a second side, and a centerpoint, said processor further programmed to gradually decrease a quantity of emission data binned into the first data bin from the centerpoint to the second of the transition region.

15. The PET imaging system of claim 9, wherein the transition region includes a first transition sub-region and a second transition sub-region, said processor further programmed to:
- bin the emission data acquired to the left of the transition region into a first data bin;
- bin the emission data acquired to the right of the transition region into a second data bin;
- bin a portion of the emission data acquired in the first transition sub-region into the first and second data bins; and
- bin a portion of the emission data acquired in the second transition sub-region into the first and second data bins.

16. The PET imaging system of claim 9, wherein the transition region has a width that is approximately twice the axial field-of-view of a detector acquiring data from the region of interest.

17. A non-transitory computer readable medium encoded with a program programmed to instruct a computer to:
- receive an input defining a scan window having a predetermined length along an examination axis of the PET imaging system, the scan window corresponding to a region of interest to be continuously scanned by the PET imaging system;
- define at least two data bins corresponding to two separate scan regions within the scan window;
- define a transition region that overlaps a portion of each of the separate scan regions within the scan window, the transition region having a width that is shorter than a length of the scan window;
- bin emission data acquired within the transition region into the two data bins;
- bin emission data acquired from outside the transition region into one of the two data bins; and
- reconstruct an image using the emission data in the two data bins.

18. The non-transitory computer readable medium of claim 17, wherein the program is further programmed to instruct the computer to reconstruct the image using the emission data within a first bin while concurrently binning emission data into a second different bin.

19. The non-transitory computer readable medium of claim 17, wherein the program is further programmed to instruct the computer to:
- bin the emission data acquired to the left of the transition region into a first data bin; and
- bin a portion the emission data acquired between the first side and the centerpoint of the transition region into the first data bin and the second data bin.

20. The non-transitory computer readable medium of claim 19, wherein the program is further programmed to instruct the computer to gradually increase a quantity of emission data binned into the second data bin from the first side to the centerpoint of the transition region.

* * * * *